United States Patent [19]

Massot et al.

[11] 4,343,784

[45] Aug. 10, 1982

[54] COMPOSITION AND METHOD EMPLOYING EXTRACTS OF HANSENULA AS A MEDICAMENT

[75] Inventors: Jacqueline O. Massot, Pontault-Combault; Jacques N. Astoin, Paris, both of France

[73] Assignee: Univablot, Paris, France

[21] Appl. No.: 241,550

[22] Filed: Mar. 9, 1981

[30] Foreign Application Priority Data

Mar. 10, 1980 [FR] France ............................... 80 05302

[51] Int. Cl.$^3$ ..................... A61K 35/78; A61K 31/70; A61K 35/72
[52] U.S. Cl. ..................................... 424/45; 424/180; 424/195
[58] Field of Search ......................... 424/195, 180, 45

[56] References Cited

FOREIGN PATENT DOCUMENTS 15175  9/1980  European Pat. Off. ............ 424/195

OTHER PUBLICATIONS

Chemical Abstracts vol. 89:161420q (1978).

Primary Examiner—Donald B. Moyer
Attorney, Agent, or Firm—Wegner & Bretschneider

[57] ABSTRACT

Medicament based on Hansenula or extracts of Hansenula.

The medicament consists of Hansenula yeasts, in particular of *Hansenula anomala*, or extracts of Hansenula, notably insoluble glucans.

7 Claims, No Drawings

COMPOSITION AND METHOD EMPLOYING EXTRACTS OF HANSENULA AS A MEDICAMENT

The subject of the present invention is the use of Hansenula, in particular *Hansenula anomala*, or extracts of Hansenula as such, as a medicament.

Hansenula are yeasts belonging to the Saccharomycetaceae family and to the Saccharomycoideae sub-family, which comprises numerous genera. These genera are defined for example in "The Yeasts" (LODDER, North Holland Publishing Company, 1970, pp. 405 to 554). The species *Hansenula anomala*, which has more especially been studied by the Applicants, is known and available in several collections of microorganisms, for example in the CENTRAALBUREAU VOOR SCHIMMEL CULTURES (DELFT, Netherlands).

As far as the Applicants know, the Hansenula have never been studied with a view to therapeutic use. Yeasts belonging to a different genus, such as *Saccharomyces cerevisiae*, have found many therapeutic applications, in particular for protecting or regenerating the intestinal bacterial flora.

In addition, some authors have studied extracts of *Saccharomyces cerevisiae* or their glucans in connection with their action of the reticulo-endothelial system (RIGGI and Di Luzio, Am. J. Physiol. (1961) 200, 2, pp. 297–300), or in connection with their anti-tumour action (HAMURO et al, C. A., (1978) 89, 40 704 b).

The Applicants have now found that the Hansenula, notably *Hansenula anomala* as well as its extracts, and in particular the insoluble glucans, possess exceptional pharmacological properties justifying their use as medicaments in the treatment of infectious diseases: nonspecific immunostimulation, potentialisation of antibiotic action, and enhancement of vaccine activity.

Hansenula strains may be kept and cultivated in a known manner on stock media and fermentation media commonly used for yeasts. The cells obtained may be dried at 50° in vacuo or, preferably, lyophilised.

The extracts according to the invention, which are mainly insoluble glucans, may be isolated from the Hansenula cell walls by, for example, the method described by Bell and Northcote (J. Chem. Soc. (1950), pp. 1944–47), if necessary modified, for example according to Peat et al (idem, 1958a, pp. 3862–3868). The principle consists of firstly removing the proteins, lipids and mannans by alkaline treatment, and then the glycogen and the soluble glucans by acid treatment, from the cellular mass obtained by fermentation.

The following examples illustrate how these products are obtained.

EXAMPLE 1

Process for fermenting *Hansenula anomala*

(a) Preparation of the yeast sediments

The yeast sediment is prepared from the stock culture of the *Hansenula anomala* strain, the latter being obtained by incubating yeast for 48 hours at 30° C. on sloped agar containing:

| Medium (1) | | |
|---|---|---|
| | yeast extract | 500 ml |
| | pancreatic peptone | 2 g |
| | starch syrup | 10 g |
| | agar | 18 g |
| | tap water, sufficient to make up | 1 liter. |

The culture is separated from the sloped agar with about 10 ml of sterile physiological serum and is sucked up with a tube. The suspension thus obtained is added in a sterile manner to a 6 liter Erlenmeyer flask containing 1.5 liters of fermentation medium having the following composition:

| Medium (2) | | |
|---|---|---|
| | glucose | 15 g |
| | yeast extract | 2.5 g |
| | ammonium sulphate | 5 g |
| | monopotassium phosphate | 5 g |
| | magnesium sulphate, $7H_2O$ | 0.05 g |
| | calcium chloride | 0.01 g |
| | ferrous sulphate, $7H_2O$ | 0.01 g |
| | potassium chloride | 0.01 g |
| | tap water, sufficient to make up | 1 liter. |

Incubation is carried out for 24 hours at 27°±1° on a rotary shaker driven at about 115 revs./minute.

(b) Fermentation

The contents of 2 Erlenmeyer flasks such as obtained above (totalling about 3 liters) are cultured in a sterile fermentation vat containing 200 liters of medium (2) described above. Fermentation is carried out for 20 hours under aeration at a rate of 20 m$^3$/hour. The contents of the vat are then centrifuged to collect the mass containing the Hansenula cells.

3.35 kg of cellular mass (moisture content 78%) is obtained.

EXAMPLE 2

Preparation of dried *Hansenula anomala* cells 220 g of cells ready for use are obtained by drying at 50° C. in vacuo, 1 kg of the cellular mass obtained in Example 1.

A variant, in which a product that is easier to keep and use can be obtained, is to lyophilise the cellular mass obtained in Example 1, and in this way 215 g of usable cells can be obtained from 1 kg of cellular mass.

EXAMPLE 3

Preparation of *Hansenula anomala* glucans 1 kg of freshly centrifuged cellular mass obtained according to Example 1 is treated with 3 liters of a 6% sodium carbonate solution for 1½ hours at 80° C.; the residue is collected by centrifugation (4000 revs./minute, for 15 minutes) and is then treated with 5 liters of a 3% sodium carbonate solution for 18 hours at ambient temperature; the suspension is recentrifuged and the insoluble product is treated once more with a 3% sodium carbonate solution for 1½ hours at 80° C. The suspension is centrifuged and the deposit is taken up in 3 liters of water. The suspension thus obtained is adjusted to a pH of 4.5 with acetic (or hydrochloric) acid and is heated at 80° C. for 2 hours while stirring. The residue obtained by centrifugation is washed 3 times, each time with 1 liter of boiling water, and is taken up in 2.5 liters of a 0.02 M solution of sodium acetate, following which it is autoclaved at 2 bars for 1 hour.

The insoluble fraction is washed with water, then with ethanol and acetone, and is dried in vacuo at a maximum temperature of 50° C. 18.3 g of a creamycoloured powder is obtained by grinding and crushing the resultant product.

An alternative procedure is to lyophilise: 15.3 g of extract is obtained in this way from the same amount of cells.

Analysis: C=46.14%; H=7.72%; O=45.52%; N=<0.4%; P: absent.

The action of pancreatic amylase on the extract releases only traces of reducing compounds, thus indicating the absence of glycogen.

The extract according to the invention is remarkable in that it is insoluble in water, alkaline or acid solutions, and in the normal organic solvents such as ethanol, diethyl ether, ethyl acetate, acetone, chloroform, etc.

Nevertheless, it is found to be very readily soluble in dimethyl sulphoxide (DMSO).

Specific rotatory power: $[\alpha]_D^{20} \simeq -65°$ ($C = 0.16$; DMSO)

Infra-red: the spectrum obtained with a KBr prism has a characteristic absorption band at 890 cm$^{-1}$.

It follows from this data that the extracts obtained from the cell wall of *Hansenula anomala* are mainly branched glucose polymers joined by a majority of $\beta$ bonds. The action of hexo-$\beta$-(1-3)-D-glucanase on the extract liberates reducing compounds, thus confirming the existence of $\beta$-(1-3) bonds. The extract according to the invention thus essentially consists of $\beta$-(1-3)-D-glucans, which will hereinafter simply be referred to as "glucans".

The Hansenula yeasts, in particular Hansenula anomala as well as the glucans extracted therefrom, have been subjected to various pharmacological tests.

TOXICITY

No toxicity was found in mice when *Hansenula anomala* or its glucans were administered orally.

When administered intra-peritoneally, the LD$_{50}$ of these glucans is greater than 500 mg/kg.

EVIDENCE OF IMMUNOSTIMULATION PRODUCED BY WHOLE HANSENULA CELLS AND BY ITS GLUCANS (1) Evidence from the consumption of the complement The increase in the consumption of the complement is a sign of immunostimulation. This test was carried out with whole *Hansenula anomala* cells administered parenterally to rabbits.

The rabbits were divided up into groups as follows:
1 control group comprising 2 rabbits
1 rabbit receiving a parenteral injection of 5 mg/kg of *Hansenula anomala*
1 rabbit receiving a parenteral injection of 1 mg/kg.

The complement consumption is measured daily. The measurement is converted into adaptation by measuring the area of haemolysis, the latter being an indication of the activity of the complement of the animals.

This test gave the following results (in areas of haemolysis).

|  | Before test | 2nd day | 3rd day | 4th day | 5th day | 8th day |
|---|---|---|---|---|---|---|
| Control group No. 1 | 25.50 | 23.75 | 29.22 | 27.33 | 27.33 |  |
| Control group No. 2 | 26.41 | 22.89 | 24.62 | 22.04 | 23.75 |  |
| Hansenula 5 mg | 29.22 | 36.32 | 50.27 | 39.60 | 33.18 | 38.18 |

-continued

|  | Before test | 2nd day | 3rd day | 4th day | 5th day | 8th day |
|---|---|---|---|---|---|---|
| Hansenula 1 mg | 34.21 | 45.36 | 55.42 | 52.81 | 47.78 | 24.62 |

As can be seen, 48 hours after the injection there is a very significant increase in the activity of the complement (+70% for 5 mg/kg; +61% for 1 mg/kg).

(2) From the protection conferred by prophylactic treatment, administered intra-peritoneally, against a lethal experimental infection The animals used are female SPF IFFA CREDO mice weighing 18–20 g, fed for 8 days before the test on a yeast-free diet but containing the necessary amount of vitamins.

The mice are distributed into 2 groups:
1 infection control group
1 infected group treated either with Hansenula or with its glucans.

The tests were carried out on mice infected intravenously with about $1 \times 10^6$ *Staphylococcus aureus* pathogens (Institut Pasteur strain 54.146) or with about $1 \times 10^4$ *Klebsiella pneumoniae*.

The treatment was given intraperitoneally.
for *Hansenula anomala*, at a dosage of 50 mg/kg
for Hansenula glucans, at a dosage of 10 mg/kg.
The experimental plan is as follows:

|  | Control group | Treated group |
|---|---|---|
| Day-7 | I.P. injection of 0.2 ml of physiological serum per mouse | I.P. injection of 0.2 ml of Hansenula or *Hansenula glucan* suspension |
| Day-4 | 2nd injection 2nd injection | 2nd injection 2nd injection |
| Day-0 | Bacterial infection | |

The number of dead mice in each group is recorded every day.

The following tables show the number of surviving animals.

| (A) - With whole yeast from *Hansenula anomala* | | |
|---|---|---|
|  | Control group | Treated group |
| Infection with *Klebsiella pneumoniae* | 1/10 | 7/9 |
| Survival % | 10% | 77% |
| Infection with *Staphylococcus aureus* | 0/10 | 7/10 |
| Survival % | 0% | 70% |

| (B) - With *Hansenula glucans* | | |
|---|---|---|
| Infection with Staphylococcus | Control group | Treated group |
| 1st test | 0/10 | 8/10 |
| 2nd test | 0/10 | 6/10 |
| 3rd test | 2/10 | 7/10 |
| 4th test | 2/10 | 5/10 |
| 5th test | 2/10 | 7/10 |
| Survival % | 12% | 66% |

As can be seen, the number of dead mice is less in the treated groups than the number of dead mice in the control groups, both when treatment is given with whole cells of *Hansenula anomala* or with its glucans.

Given the virulence of the injected pathogen, a very high degree of protection is conferred by an I.P. injection of Hansenula or its glucans. This protection can be attributed to a non-specific immunostimulation.

EVIDENCE FOR IMMUNOSTIMULATION BY *HANSENULA ANOMALA* AND ITS GLUCANS AFTER PREVIOUS INJECTION OF ANTIGEN

The animals used are female SPF IFFA CREDO mice weighing 18–20 g, fed for one week before the experiments on a yeast-free diet but containing the necessary amount of vitamins.

The mice are divided into 5 groups:
group 1: infection control group
group 2: antigen control group ("vaccine" group)
group 3: receiving antigen+infection
group 4: as group 3, but in addition treated with *Hansenula anomala*
group 5: as group 3, but in addition treated with Hansenula glucans.

The antigen in this case consists of a non-lethal dose of a *Staphylococcus aureus* culture (Institut Pasteur 54.146).

The culture obtained from 16 hours in nutrient broth is diluted at the moment of vaccination to $1 \times 10^{-4}$, representing about $1 \times 10^4$ germs/ml.

The mice of groups 1 and 3 to 5 are infected by the highly pathogenic reactivated *Staphylococcus aureus* strain (Institut Pasteur 54.146). A culture in nutrient broth incubated for 16 hours at 37° is firstly diluted to 1/100 in physiological serum (i.e. $1 \times 10^7$ germs/ml) and is then injected intravenously to infect the mice.

The experimental plan is as follows:

|  | Group 1 Infection control group | Group 2 Vaccine control group | Group 3 Vaccine + infection | Group 4 As 3+ Hansenula 1a | Group 5 As 3+ Hansenula glucans |
|---|---|---|---|---|---|
| Day-9 | 0.2 ml I.V. of physiological serum | 0.2 ml I.V. of $10^4$ germs/ml (vaccine) | | | |
| Day-6 to Day-1 | | 0.2 ml I.P. of physiological serum per day | | 0.2 ml I.P. of 50 mg/kg Hansenula 1a | 0.2 ml I.P. 10 mg/kg glucans |
| Day 0 | Infection ($10^6$ germs) 0.2 ml I.V. | Physiological serum, 0.2 ml I.V. | I.V. infection with 0.2 ml ($10^6$ germs) 0.2 ml group 1 | | |

The number of dead mice in each group is recorded every day. The survivors in each group were as follows:

| vaccine innocuousness control group | 9/9, i.e. 100% survival |
|---|---|
| infected control group of mice | 2/10 i.e. 20% survival |
| vaccinated and infected mice | 4/9, i.e. 44% survival |
| mice additionally treated with Hansenula | 9/10, i.e. 90% survival |
| mice additionally treated with glucans | 9/10, i.e. 90% survival |

These results show that there is an 80% mortality among the animals infected with $10^6$ *Staphylococcus aureus*. Animals that have been vaccinated once 9 days before infection are partially protected, the mortality then being 44%. As may be seen, vaccination combined with a treatment with Hansenula or its glucans administered intraperitoneally greatly reduces the mortality, in fact down to 10%.

Given the extreme virulence of the injected pathogens, a high degree of potentialisation were conferred by the glucans on a specific prevaccination. This potentialisation can be attributed to an immunostimulation.

EVIDENCE FOR THE POTENTIALISATION OF THE ACTION OF ANTIBIOTICS

In this test, a treatment with antibiotics (tetracycline hydrochloride for 4 days, at a dosage of 10 mg/kg) is combined with a prophylactic treatment consisting of 2 injections of glucans at a dosage of 10 mg/kg.

The animals used are the same strain as in the previous tests, and are on the same diet.

The mice are distributed into 4 groups, each of 10 mice:
group 1: infected control group
group 2: treated with Hansenula glucans
group 3: treated with 10 mg/kg per day of tetracycline
group 4: receiving Hansenula glucans and 10 mg/kg per day of tetracycline.

The test was carried out on mice infected intravenously with about $1 \times 10^6$ reactivated *Staphylococcus aureus* pathogens (Institut Pasteur 54.146).

A culture in nutrient broth incubated for 16 hours at 37° C. is firstly diluted to 1/100 and is then used to infect the mice.

The experimental plan is as follows:

|  | Infected control group | Glucans | Tetracycline | Tetracycline + glucans |
|---|---|---|---|---|
| Day-7 to Day-4 | I.P.: 0.2 ml of physiological serum | I.P.: 0.2 ml of *glucans*, 10 mg/kg | As per control group | I.P.: 0.2 ml of *glucans*, 10 mg/kg |
| Day 0 | | I.V. infection with Staphylococci | | |
| Day + 1 to Day + 4 | Orally: 0.2 ml of physiological serum | Orally: as per control group | Orally: 0.2 ml of tetracycline | Orally: 0.2 ml of tetracycline |

The number of dead mice is recorded every day. The following table shows the number of surviving mice found in each group.

| Control group | Glucans alone | Tetracycline | Glucans + tetracycline |
|---|---|---|---|
| 1/10 | 3/10 | 2/10 | 4/10 |

As previously, a certain degree of protection was conferred by Hansenula glucans alone. Tetracycline at this dosage conferred a small degree of protection on the animals (2/10). The combination of glucans with the same dosage of tetracycline potentialised the antibiotic effect of the latter (4/10).

The tests illustrated above showed that the administration of *Hansenula anomala* or its glucans on the one hand reduces, by non-specific immunostimulation, the mortality of animals infected by pathogens and, on the other hand, potentialises the action of the antibiotic and vaccines. This yeast can thus be used to reinforce the resistance of an organism to infection and to improve the immune defence system.

The *Hansenula anomala* yeasts and the glucans extracted therefrom are non-toxic and can thus be used to prevent and/or treat acute or chronic infections, in particular oto-rhino-laryngeal and/or pulmonary infections, and also any other disease or infection of viral or bacterial origin. *Hansenula anomala* and its glucans can be used as medicaments, either alone or in combination with one or more antigens or also in combination with one or more antibiotics.

Whole Hansenula cells may be administered orally in daily dosages of 100 to 2000 mg (dry product), preferably in capsules containing the lyophilised cells and, if necessary, conventional excipients, or also in ampoules for oral administration, the cells being suspended in their culture medium.

| Example of composition of a capsule: | |
|---|---|
| Lyophilised cells of *Hansenula anomala* | 50 mg |
| Lactose | 7 mg |
| Magnesium stearate | 2 mg |
| Icing sugar, in an amount sufficient for a capsule of | 150 mg |

The Hansenula glucans may also be administered orally in daily dosages of 20 to 500 mg, or may be used in the form of suspensions for injection, at a dosage of 5 to 100 mg per day. The use of these glucans in the form of skin creams or aerosols is also possible.

| Example of the composition of a suspension for injection: | |
|---|---|
| Micronised *Hansenula anomala* glucans* | 0.010 g |
| Polysorbate 80 | 0.025 g |
| Polyvinylpyrrolidone | 0.025 g |
| Monosodium phosphate | 0.025 g |
| Sodium chloride, sufficient to be isotonic with sodium merthiolate | 0.0002 g |
| Pyrogen-free distilled water, in amount sufficient for 1 5 ml ampoule for injection | |

*(particles) <50 μm, of which 80% <10 μm).

| Example of the composition of an aerosol: | |
|---|---|
| Micronised *glucans* | 0.050 g |
| Polysorbate 80 | 0.2 g |
| Polyoxyethylenated oleic glycerides | 1 g |
| Monosodium phosphate | 0.1 g |
| Sodium chloride, in an amount isotonic with sodium merthiolate | 0.0008 g |
| Purified water, in an amount sufficient to make up | 20 ml. |

We claim:

1. A therapeutic composition for the treatment of infection which contains as active ingredient a therapeutically effective amount of an extract of water-insoluble Hansenula glucans prepared by extracting cells of Hansenula with alkali to remove proteins, lipids, and mannans and with acid to remove glycogens and soluble glucans, as well as a pharmaceutically acceptable excipient.

2. Medicament according to claim 1, characterised in that the insoluble glucans are essentially β-(1-3)-D-glucans.

3. A composition according to claim 1, containing 20-500 mg of the glucans in an oral dosage form.

4. A composition according to claim 1, containing 5-100 mg of the glucans, in an injectable suspension.

5. A composition according to claim 1 in aerosol form.

6. The process for treating infection in a patient which comprises oral administration of 20-500 mg/day of an extract of water-insoluble Hansenula glucans prepared by extracting cells of Hansenula with alkali to remove proteins, lipids and mannans and with acid to remove glycogens and soluble glucans.

7. The process of treating infection in a patient which comprises parenteral administration of an injectable suspension of 5-100 mg/day of water-insoluble glucans of Hansenula prepared by extracting cells by Hansenula with alkali to remove proteins, lipids and mannans and with acid to remove glycogens and soluble glucans.

* * * * *